United States Patent [19]

Habata et al.

[11] 3,983,180

[45] Sept. 28, 1976

[54] PROCESS FOR PREPARING METHYL CHLORIDE

[75] Inventors: Kiichi Habata, Annaka; Shozo Tanaka, Osaka; Hitoyuki Araki, Annaka, all of Japan

[73] Assignee: Shinetsu Chemical Company, Tokyo, Japan

[22] Filed: Oct. 2, 1974

[21] Appl. No.: 511,208

[30] Foreign Application Priority Data

Oct. 6, 1973  Japan.............................. 48-112723

[52] U.S. Cl. ............................................... 260/657
[51] Int. Cl.² ......................................... C07C 17/00
[58] Field of Search ..................................... 260/657

[56] References Cited
UNITED STATES PATENTS

| | | | |
|---|---|---|---|
| 2,153,170 | 4/1939 | Buc et al............................. | 260/657 |
| 2,244,629 | 6/1941 | Livak et al.......................... | 260/657 |

FOREIGN PATENTS OR APPLICATIONS

| | | | |
|---|---|---|---|
| 691,295 | 7/1964 | Canada............................... | 260/657 |

*Primary Examiner*—Delbert E. Gantz
*Assistant Examiner*—Joseph A. Boska
*Attorney, Agent, or Firm*—Toren, McGeady and Stanger

[57]  ABSTRACT

A process for preparing methyl chloride by reacting hydrogen chloride with methanol in the liquid-phase non-catalytic reaction, employing a reaction system comprising a reactor and two distillation columns, each being operated under a different pressure, to greatly increase the space time yield and the conversion of hydrogen chloride and methanol, and at the same time to reduce the production of dimethyl ether as a byproduct. The raw materials used may be either gaseous or liquid; they may contain a large amount of water or gases insoluble in water. By this process, hydrogen chloride gas and diluted hydrochloric acid that are produced as a byproduct or waste in various chemical processes can be effectively utilized.

3 Claims, 1 Drawing Figure

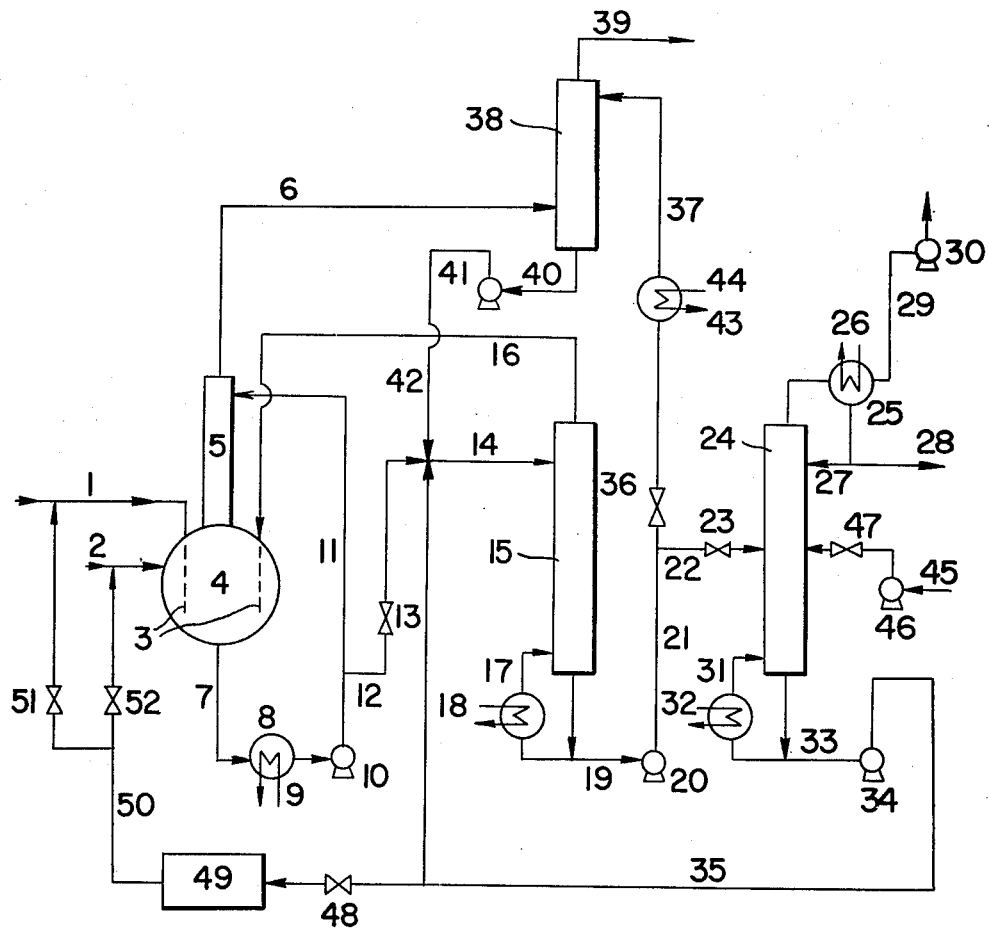

PROCESS FOR PREPARING METHYL CHLORIDE

FIELD OF THE INVENTION

The present invention relates to be process for preparing methyl chloride from hydrogen chloride and methanol.

DESCRIPTION OF THE PRIOR ART

Various reports have been made public on the methods for preparing methyl chloride by reacting hydrogen chloride with methanol. Typical methods commercially employed at present are: (1) the vaporphase catalytic method in which hydrogen chloride is reacted with methanol in vapor phase in the presence of a catalyst, such as, alumina, (2) the liquid-pahse catalytic method in which hydrogen chloride is reacted with methanol in liquid phase in the presence of a catalyst, such as, zinc chloride, and (3) the liquid-phase non-catalytic method in which hydrogen chloride is reacted with methanol in liquid phase in the absence of any catalyst.

All these methods have not been freed from any drawbacks. For example, speaking of the vapor-phase catalytic method, it is carried out at a high temperature, say, from 300° to 450°C and, consequently, dimethyl ether is formed as a byproduct in a greater amount than in the other two methods. In addition, the catalyst used is required to be replaced or regenerated, and as to the raw materials, hydrogen chloride must be in the gaseous anhydrous or a nearly anhydrous state and methanol must be in the gaseous state.

Speaking next of the liquid-phase catalytic method, it is carried out at a higher temperature compared to the liquid-phase non-catalytic method. Due to operation at such a high temperature and the use of a catalyst, dimethyl ether is produced in a greater amount than in the liquid-phase non-catalytic method. Moreover, water contained in the raw materials and water generated by the reaction have to be removed by evaporation. Sometimes, more heat is required than in the other methods. In order to recover the unreacted hydrogen chloride and methanol vaporized along with the water, some additional facilities are required.

Next, according to the conventional liquid-phase non-catalytic method, in which less dimethyl ether is formed than in any of the other two methods, the rate of the reaction between hydrogen chloride and methanol is so low that a large reaction space is required, and in order to increase the conversion, the provision of facilities for recovering any unreacted hydrogen chloride and methanol becomes indispensable.

The conventional liquid-phase non-catalytic method will be described in detail in the following. In order to attain a high space time yield and a high conversion by the method of this type, the reaction rate is enhanced by increasing the concentration of the reactants in the reaction mixture in a reactor and, at the same time, the unreacted reactants coming out of the reactor accompanied by the reaction product are separated from the product by means of recovering facilities, such as, distillation columns and are recycled to the reactor. One should bear in mind when practicing the liquid-phase non-catalytic method for the preparation of methyl chloride from hydrogen chloride and methanol that, in the binary system of hydrogen chloride and water or in the ternary system of hydrogen chloride, water and methanol, there exists the maximum boiling point azeotrope with the azeotropic compositions corresponding to the pressures. If hydrogen chloride is subjected to reaction with methanol until its concentration becomes lower than the azeotropic composition in the reactor, the reaction mixture discharged from the reactor can be separated into hydrochloric acid of the above-mentioned nearly azeotropic composition, nearly pure methanol and nearly pure water by means of recovering facilities composed of, for example, two distillation columns. Consequently, the former two substances can be recycled to the reactor and the latter can be discharged out of the reaction system to, thereby attain a high conversion. However, the concentration of hydrogen chloride in the reactor, in this case, is lower than the azeotropic composition, so that the reaction rate is low and the reactor is required to have a large volume.

Further, when the reaction is carried out in such a manner as to make the concentration of hydrochloric acid in the reactor higher than the azeotropic composition, it proceeds at a high rate, and the volume of the reactor can be made small, guaranteeing a high space time yield. But, in this case where the concentration of hydrogen chloride is higher than the azeotropic composition, only part of the hydrogen chloride and methanol to be recycled to the reactor can be separated by an ordinary distillation from the reaction mixture discharged from the reactor, and water can not be separated as pure water, but separated as hydrochloric acid of a nearly azeotropic composition. Therefore, in order to discharge water out of the reaction system, the hydrochloric acid of a nearly azeotropic composition is discharged at the sacrifice of a large amount of hydrogen chloride. Consequently, it is impossible to obtain a high conversion by this method. In order to prepare methyl chloride at a high space time yield and a high conversion from hydrogen chloride and methanol by the liquid-phase non-catalytic method, firstly, the concentration of hydrogen chloride in the reactor should be maintained higher than the azeotropic composition and, secondly, special recovery facilities should be provided for separating the reaction mixture above the azeotropic composition with respect to hydrogen chloride into hydrogen chloride, methanol and water, and for recycling the former two substances back to the reactor and discharging the latter out of the system.

In one of the means to separate hydrochloric acid above azeotropic composition into hydrogen chloride and water, an electrolyte, such as, calcium chloride or sulfuric acid is added for the purpose of lowering the azeotropic composition of hydrochloric acid. When hydrochloric acid above the azeotropic composition is distilled with addition of the aqueous solution of such an electrolyte, vapor rich in hydrogen chloride and an aqueous solution of the electrolyte containing hydrogen chloride in very low concentration are obtained. Water is evaporated from the electrolyte solution and condensed to be discharged as water containing little hydrogen chloride. Consequently, a combination of a reactor, in which the concentration of hydrogen chloride is maintained above the azeotropic composition, and recovery facilities comprising an azeotropic distillation column utilizing the above electrolyte is required for the preparation of methyl chloride by the liquid-phase non-catalytic method with a high space time yield and a high conversion. However, this process is not always advantageous, because in order to keep the concentration of hydrogen chloride above the azeotropic composition and the temperature of the reactor at a point sufficient to give a satisfactory reaction rate, a pressurized reactor vessel should be employed. When an azeotropic distillation column, into which an electrolyte as mentioned above is added, is operated at the atmospheric pressure, the vapor rich in hydrogen chloride and methanol, obtained at the column top, should be pressurized by a pump after having been liquefied by condensation or absorption, or should be directly pressurized by use of a compressor before it is recycled into the reactor vessel kept in pressurized state.

When the former method, i.e., pressurization after liquefaction, is employed, losses in thermal energy and cooling capacity are unavoidable since the vapor once formed by the heat in put in the azeotropic distillation column is liquefied to be recycled to the reactor and there heated again up to the appropriate reaction temperature. Therefore, the method is disadvantageous in comparison with the liquid-phase catalytic method in which the reaction and the azeotropic distillation take place simultaneously in one reactor vessel with less consumption of thermal energy and cooling capacity. The direct compression method is also disadvantageous because of the requirement of a corrosion-resistant compressor as well as the problems caused by the condensation of the vapor.

Alternatively, the azeotropic distillation column may be kept at a higher pressure than the reactor so that the vapor collected from the top of the distillation column may be recycled directly to the reactor by means of some devices such as a sparger. But, the azeotropic distillation column in which a concentrated solution of the electrolyte is boiled is operated at a temperature high enough to boil the solution under high pressure, the temperature becoming even higher by 10° to 50°C by the presence of the electrolyte than it otherwise would.

OBJECTS OF THE INVENTION

An object of the present invention is to improve the liquid-phase non-catalytic method so as to provide a more reasonable and economical process for preparing methyl chloride from hydrogen chloride and methanol. Another object of the present invention is to provide a process in which the conversion of hydrogen chloride and methanol and the space time yield are remarkably increased and the production of dimethyl ether as a byproduct is much reduced by employing a reaction system composed of a reactor and two distillation columns, those composing units being operated under different pressures. Still another object of the present invention is to provide a process in which hydrogen chloride gas and diluted hydrochloric acid produced as a byproduct or waste in various other chemical processes can be effectively utilized.

SUMMARY OF THE INVENTION

According to the present invention, a process for preparing methyl chloride by reacting hydrogen chloride with methanol in the absence of any catalysts in liquid phase is carried out with a reaction system comprising (1) a reactor maintained at pressure higher than the atmospheric pressure and supplied with a reaction mixture consisting of hydrogen chloride and methanol, (2) a first distillation column maintained at pressure higher than that of the reactor and (3) a second distillation column maintained at a pressure lower than that of the first distillation column, the process comprising the steps of a. withdrawing part of the reaction mixture from the reactor,
b. introducing the reaction mixture thus withdrawn into the first distillation column,
c. collecting from the top of the first distillation column vapor richer in hydrogen chloride and methanol than the reaction mixture in the reactor,
d. recycling the vapor thus collected to the reactor,
e. withdrawing from the bottom of the first distillation column a mixture lower in hydrogen chloride and methanol concentrations than the reaction mixture contained in the reactor,
f. discharging from the top of the second distillation column water contained in the raw materials and water generated during the reaction,
g. withdrawing from the bottom of the second distillation column a mixture richer in hydrogen chloride than the mixture in the bottom of the first distillation column,
h. recycling the mixture thus withdrawn to the first distillation column or to the reactor, and
i. collecting methyl chloride formed in the reactor from its top.

BRIEF DESCRIPTION OF THE DRAWING

In the accompanying drawing, the single FIGURE is one form of flowsheet embodying the invention.

DESCRIPTION OF THE PREFERRED EMBODIMENT

Referring now more particularly to the drawing, the process of the invention will be described hereinafter.

When the raw materials are gaseous, they are introduced into reactor 4 by means of conduit 1 and sparger 3, while, when they are liquid, they are introduced into reactor 4 by means of conduit 2. Reactor 4 contains a reaction mixture composed of hydrochloric acid and methanol in which the concentration of hydrogen chloride is above the azeotropic composition so that the reaction may be carried out at a high rate, and a high space time yield may be guaranteed. The reaction mixture in reactor 4 is maintained at 90°C or above, so as to able to attain a sufficient reaction rate, and at a pressure above atmospheric pressure, preferably in the range between 1 and 3 kg/cm²G, so as to prevent the evaporation of hydrogen chloride and methanol. Methyl chloride formed is collected from the top of reactor 4 by means of first absorption column 5, conduit 6, and second absorption column 38.

For the purpose of discharging water contained in the raw materials and generated during the reaction, part of the reaction mixture in reactor 4 is withdrawn by means of conduit 7, cooler 8, pump 10 and conduit 12, while the level of the liquid surface in reactor 4 is kept constant by means of valve 13. Then, through conduit 14, the withdrawn mixture is sent to first distillation column 15. The pressure in first distillation column 15 is a little higher than that of reactor 4 or, higher exactly by 0.1 – 1 kg/cm²G. The difference can be more than 1 kg/cm²G, but any such difference is not a requirement. Vapor richer in hydrogen chloride and methanol than the reaction mixture in reactor 4 is collected from the top of first distillation column 15 and then recycled to reactor 4 through conduit 16 and sparger 3, while from the bottom of first distillation column 15 by way of conduit 19 hydrochloric acid is taken out which is nearly of the azeotropic composition under the pressure of first distillation column 15, and contains little methanol. The hydrochloric acid thus taken out from first distillation column 15 is sent by means of pump 20, conduits 21 and 22, and valve 23 to second distillation column 24, which is kept at a lower pressure than first distill column 15. The azeotropic composition of hydrochloric acid varies according to the pressure under which it is placed. The higher is the pressure, the lower is the hydrogen chloride concentration in the azeotropic mixture. Therefore, if there is a proper difference in pressure between first distillation column 15 and second distillation column 24, hydrochloric acid withdrawn from the bottom of first distillation column 15 and sent to second distillation column 24 would be lower in hydrogen chloride concentration than the azeotropic composition under the pressure inside second distillation column 24. Consequently, when proper refluxing is carried out in second distillation column 24, water containing only a small amount of hydrogen chloride is discharged through the top of the column. The pressure of second distillation column 24 must be lower than that of first distillation column 15. In an ordinary operation, it is advisable that the pressure of second distillation column 24 should be from 10 to 500 mmHg (absolute).

It should be noted that the hydrochloric acid withdrawn from the bottom of first distillation column 15 contains little methanol, so that the water discharged from the top of second distillation column 24 contains little methanol.

A condenser 25 is installed for the purpose of refluxing or distilling out the vapor from the top of second distillation column 24, and vacuum pump 30 for reducing, when necessary, the pressure of second distillation column 24. From the bottom of the second distillation column 24 is obtained hydrochloric acid, which is nearly of the azeotropic composition under the pressure of the column.

The reaction system must be designed and operated so that the mixture kept in the bottom of first distillation column 15 is made lower in hydrogen chloride concentration than those in reactor 4 and in the bottom of second distillation column 24. The hydrochloric acid from the bottom of second distillation column 24 is recycled to first distillation column 15 by means of conduit 33, pump 24 and conduits 35 and 14.

Further, the process of the invention can find ways thereby to reuse any hydrogen chloride produced as a byproduct or waste in various other chemical processes involving the manufacture of chloromethanes and silicones. Part or whole of the relatively diluted hydrochloric acid from the bottom of second distillation column 24 is introduced by way of valve 48 into an apparatus denoted by 49 which functions as an absorber in one case and into which waste hydrogen chloride from other chemical plants is introduced, and the hydrochloric acid enriched in hydrogen chloride is supplied to reactor 4 by way of conduit 50, valve 52 and conduit 2. In particular, in the manufacture of silicones, apparatus 49 also serves as a hydrolyzer for organochlorosilanes, in which the organochlorosilanes are hydrolyzed to liberate hydrogen chloride and to consume water contained in the dilute hydrochloric acid, advantageously resulting in reduction in the quantity of the water discharged from second distillation column 24.

Part of the mixture in the bottom of first distillation column 15, which mixture is lower in hydrogen chloride concentration than that contained in the reactor 4 and contains little methanol, is collected through valve 36, cooled by cooler 43, and introduced through conduit 37 into second absorber 38 as the absorption medium, where it can absorb a small amount of hydrogen chloride and methanol accompanied by methyl chloride introduced through conduit 6. The mixture enriched in hydrogen chloride and methanol can be introduced once more into first distillation column 15 through conduit 40, pump 41 and conduits 42 and 14. Reboilers 17 and 31 are for first and second distillation columns 15 and 24, respectively.

In the conventional liquid-phase non-catalytic method where hydrogen chloride is an aqueous solution while methanol is liquid, the reactor is endothermic, requiring heat, whereas in the case of the reactor of the present invention, the vapor coming out of the top of first distillation column 15 with a large amount of heat content provided by reboiler 17 is introduced into reactor 4, and latent heat from the condesation and absorption of the vapor serves as the heat of reaction, so that the reactor is always exothermic and must be cooled. Therefore, part of the reaction mixture contained in reactor 4 is collected by means of conduit 7, cooler 8, pump 10 and conduit 11, so as to be cooled and recycled to first absorber 5, installed on top of reactor 4 for the purpose of controlling the reaction temperature. At the same time, hydrogen chloride and methanol accompanied by methyl chloride formed in reactor 4 can be absorbed in absorber 5 by the reaction mixture circulating from the reactor as the absorption medium, and recycled to reactor 4. When hydrogen chloride employed as the raw material is hydrochloric acid of low concentration, it is advisable to supply it to second distillation column 24 by means of conduit 45, pump 46 and valve 47, instead of to reactor 4. As a matter of course, the raw material hydrochloric acid or hydrogen chloride gas may be introduced at various positions other than the second distillation column 24 into the reaction system depending on its concentration.

As will be clear from the following examples that the method of the present invention guarantees a high space time yield and a high conversion regardless of the raw materials being gaseous or liquid, even when a large quantity of water is contained therein. What is better, according to the process of the invention, is that the production of dimethyl ether as a byproduct is much less than by the conventional vapor-phase or liquid-phase catalytic methods.

EXAMPLE 1

A mixture of commercially available concentrated hydrochloric acid, methanol and water in a ratio of 10:1:5 by weight was introduced into reactor 4 and the bottom of first distillation column 15. The mixture in the bottom of first distillation column 15 was evaporated in reboiler 17 by heat provided by heating medium 18.

The vapor from the top of first distillation column 15 was sent to reactor 4. The reaction mixture withdrawn from reactor 4 was cooled in cooler 8 by cooling water 9, and then the cooled mixture was recycled through pump 10 and conduit 11 so that all the vapor coming out of the top of first distillation column 15 was absorbed and liquefied in reactor 4 and absorber 5 by the recycling mixture to be sent back to first distillation column 15 through conduit 12, valve 13, and conduit 14. The pressure inside reactor 4 was maintained at 2 kg/cm²G by the help of nitrogen gas introduced through conduit 1. As a result, a mixture containing 18.2 percent by weight of hydrogen chloride and 0.05 percent by weight of methanol was obtained from the bottom of first distillation column 15.

Part of the mixture in the bottom of first distillation column 15 was withdrawn by means of conduit 19, pump 20, conduit 21, and valve 36. After the mixture thus withdrawn was cooled in cooler 43 by cooling water 44, it was sent to second absorber 38, and then recycled to first distillation column 15 by means of conduit 40, pump 41 and conduits 42 and 14.

On the other hand, a mixture of commercially available concentrated hydrochloric acid and water in a ratio of 1:1 by weight was introduced into second distillation column 24. While the pressure of the column was kept at 160 mmHg (absolute) by means of vacuum pump 30, heating medium 32 was passed through reboiler 31 and cooling water through a condenser 25 so that the batch-wise distillation was carried out. The refluxing mixture to the column proved to consist of water containing 0.5 percent by weight of hydrogen chloride, and that in the bottom of the column proved to consist of hydrochloric acid containing 22 percent by weight of hydrogen chloride.

Into the system in which a steady state had been established as described above with the total refluxing in second distillation column 24 and between first distillation column and reactor 4 were supplied 1,000 g/hour of methanol in the liquid state and 1,140 g/hour of anhydrous hydrogen chloride gas through conduit 2 and conduit 1, respectively. The temperature in reactor 4 was maintained constantly at 105°C, at which the hightest efficiency of the process was to be obtained, by controlling the circulating flow through conduit 11. Part of the mixture from the bottom of first distillation column 15 was sent to second distillation column 24, while the level of the liquid surface in the bottom of first distillation column 15 was kept constant by means of valve 23, and the mixture in the bottom of second distillation column 24 was withdrawn approximately at a constant rate and sent back to first distillation column 15 by means of pump 34 and conduits 35 and 14. In the meantime, water condensed in condenser 25 was discharged through conduit 28, while the level of the liquid surface in the bottom of column 24 was kept constant. The results are shown in the table to be set forth at the end of this series of examples.

EXAMPLE 2

In the same procedure in Example 1, 3,260 g/hour of commercially available concentrated hydrochloric acid was introduced into the system through conduit 2 instead of 1,140 g/hour of anhydrous hydrogen chloride gas introduced through conduit 1. The results are shown in the same table.

EXAMPLE 3

In the same procedure as in Example 1, 7,600 g/hour of diluted hydrochloric acid containing 15 percent by weight of hydrogen chloride was introduced into second distillation column 24 by means of conduit 45, pump 46 and valve 47, instead of 1,140 g/hour of anhydrous hydrogen chloride gas introduced through conduit 1. The results are shown in the same table.

EXAMPLE 4

In the same procedure as in Example 1, 1,000 g/hour of gaseous methanol was introduced through conduit 1 instead of 1,000 g/hour of liquid methanol introduced through conduit 2. The results are shown in the same table.

| Example No. | 1 | 2 | 3 | 4 |
|---|---|---|---|---|
| State of hydrogen chloride as used | Anhydrous gas | Aqueous solution | Aqueous solution | Anhydrous gas |
| Concentration of hydrogen chloride, % by weight | 99.5< | 35 | 15 | 99.5< |
| State of methanol as used | Liquid | Liquid | Liquid | Gas |
| Concentration of methanol, % by weight | 99.3< | 99.3< | 99.3< | 99.3< |
| Amount of hydrogen chloride supplied, g/hour | 1140 | 3260 | 7600 | 1140 |
| Amount of hydrogen chloride supplied, calculated as anhydrous gas, g/hour | 1140 | 1140 | 1140 | 1140 |
| Amount of methanol, g/hour | 1000 | 1000 | 1000 | 1000 |
| Reaction temperature, °C | 105 | 105 | 105 | 105 |
| Pressure of the first distillation column, kg/sq.cmG | 2 | 2 | 2 | 2 |
| Pressure of the second distillation column, mmHg (absolute) | 160 | 160 | 160 | 160 |
| Production rate of methyl chloride, g/hour | 1560 | 1550 | 1550 | 1560 |
| Conversion of: Hydrogen chloride,% | 99 | 98 | 98 | 99 |
| Methanol, % | 99 | 98 | 98 | 99 |
| Dimethyl ether produced as byproduct, based on the weight of methyl chloride produced, % by weight | 0.2 | 0.1 | 0.1 | 0.2 |
| Space time yield, kg/cu.m per hour* | 150 | 130 | 125 | 150 |

*Space time yield expressed as kg of methyl chloride produced per cubic meter of the reactor volume per hour of the reaction time.

What is claimed is:

1. In a process for preparing methyl chloride by reacting a reaction mixture of hydrogen chloride with methanol in the absence of any catalysts in liquid phase, the improvement which consist essentially of:
   a. reacting the reaction mixture in a reactor maintained at a pressure in the range from 1 to 3 kg/cm²G;
   b. withdrawing a part of the reaction mixture from the reactor;
   c. introducing a first portion of said withdrawn part of the reaction mixture to a first separate distillation column which is maintained at a pressure which is at least 0.1 kg/cm²G higher than the pressure of the reactor;

d. collecting from the top of the first distillation column a vapor which is richer in hydrogen chloride and methanol than the reaction mixture;
e. recycling the collected vapor from step (d) to the reactor;
f. withdrawing from the bottom of the first distillation column a mixture which is lower in hydrogen chloride and methanol concentration than the reaction mixture and introducing a part of mixture to a second separate distillation column which is maintained at a pressure from 10 to 500 mmHg absolute;
g. discharging from the top of the second distillation column water contained in the hydrogen chloride and methanol and water generated during the reaction;
h. withdrawing from the bottom of the second distillation column a mixture richer in hydrogen chloride than the mixture in the bottom of the first distillation column;
i. recycling the mixture thus withdrawn to the first distillation column or to the reactor;
j. passing a second and remaining portion of the withdrawn part from step (b) through an absorber and into the reactor while concurrently withdrawing methyl chloride formed in the reactor from its top and passing the methyl chloride through said absorber in counter current flow to said remaining portion to absorb the hydrogen chloride and methanol from the methyl chloride, and then collecting the methyl chloride.

2. The process of claim 1 wherein the collected methyl chloride is passed into a second absorber in counter current flow with the mixture from the bottom of the first distillation column which acts as an absorption medium.

3. The process of claim 1 wherein hydrochloric acid which is more dilute than the azeotropic composition at the pressure of the first distillation column is first introduced into the second distillation column.

* * * * *